United States Patent
Elbe et al.

(10) Patent No.: US 7,314,958 B2
(45) Date of Patent: Jan. 1, 2008

(54) PHENYLBENZAMIDES

(75) Inventors: Hans-Ludwig Elbe, Wuppertal (DE); Heiko Rieck, Foy lés Lyon (FR); Ralf Dunkel, Monheim (DE); Paul Reinecke, Leverkusen (DE); Ulrike Wachendorff-Neumann, Neuwied (DE); Astrid Mauler-Machnik, Leichlingen (DE); Karl-Heinz Kuck, Langenfeld (DE)

(73) Assignee: Bayer CropScience AG, Monheim (DE)

( * ) Notice: Subject to any disclaimer, the term of this patent is extended or adjusted under 35 U.S.C. 154(b) by 0 days.

(21) Appl. No.: 10/518,446

(22) PCT Filed: Jun. 20, 2003

(86) PCT No.: PCT/EP03/06512

§ 371 (c)(1),
(2), (4) Date: Sep. 20, 2005

(87) PCT Pub. No.: WO2004/005242

PCT Pub. Date: Jan. 15, 2004

(65) Prior Publication Data

US 2006/0211771 A1   Sep. 21, 2006

(30) Foreign Application Priority Data

Jul. 2, 2002   (DE) ............... 102 29 595

(51) Int. Cl.
*C07C 233/00*   (2006.01)
(52) U.S. Cl. ............ 564/176; 564/305; 564/469; 504/149
(58) Field of Classification Search ......... 564/305; 504/147
See application file for complete search history.

(56) References Cited

U.S. PATENT DOCUMENTS 5,965,774 A * 10/1999 Yoshikawa et al. ......... 564/305

FOREIGN PATENT DOCUMENTS

| DE | 27 30 620 | 1/1979 |
| EP | 0 086 111 | 8/1983 |
| EP | 0 545 099 | 6/1993 |
| EP | 0 824 099 | 2/1998 |
| WO | 03/010149 | 2/2003 |

* cited by examiner

*Primary Examiner*—Deborah D. Carr
(74) *Attorney, Agent, or Firm*—Richard E. L. Henderson

(57) ABSTRACT

This invention relates to novel phenylbenzamides of the formula (I)

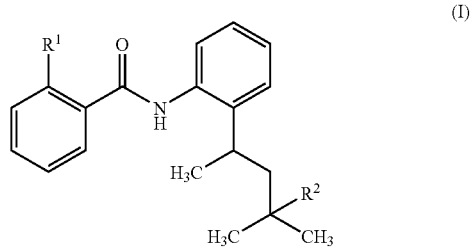

in which
  $R^1$ represents trifluoromethyl, chlorine, bromine or iodine and
  $R^2$ represents hydrogen, methyl or ethyl,
to a process for preparing these substances and their use for controlling unwanted microorganisms, and to novel intermediates and their preparation.

9 Claims, No Drawings

PHENYLBENZAMIDES

The present patent application has been filed under 35 U.S.C. 371 as a national stage application of PCT/EP2003/006512, filed Jun. 20, 2003, which was published in German as International Patent Publication WO 2004/005242 on Jan. 15, 2004, which is entitled to the right of priority of German Patent Application 102 29 595.6, filed Jul. 2, 2002.

The present invention relates to novel phenylbenzamides, to a process for their preparation and their use for controlling unwanted microorganisms.

It is already known that numerous phenylbenzamides have fungicidal properties (cf., for example, EP-A 0 545 099). Thus, for example, the phenylbenzamides N-(2-hexylphenyl)-2-(trifluoromethyl)benzamide and N-(2-hexylphenyl)-2-iodobenzamide are already known from EP-A 0 545 099, but the patent application mentioned does not contain any data on their biological activity.

There have now been found novel phenylbenzamides of the formula (I)

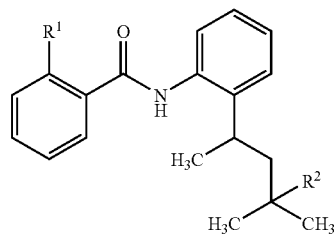

(I)

in which
R$^1$ represents trifluoromethyl, chlorine, bromine or iodine and
R$^2$ represents hydrogen or methyl,
R$^2$ furthermore represents ethyl.

Furthermore, it has been found that the phenylbenzamides of the formula (I) are obtained when
a) in a first step, aniline is reacted with an alkene of the formula (II)

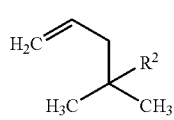

(II)

in which
R$^2$ represents hydrogen or methyl,
R$^2$ furthermore represents ethyl,
in the presence of a base and in the presence of a Lewis acid, and the resulting alkylphenylamine derivative of the formula (III)

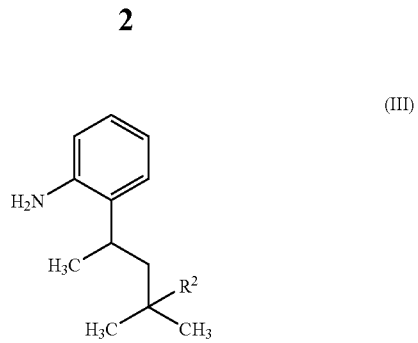

(III)

in which
R$^2$ represents hydrogen or methyl,
R$^2$ furthermore represents ethyl,
b) is, in a second step reacted with a benzoyl chloride of the formula (IV)

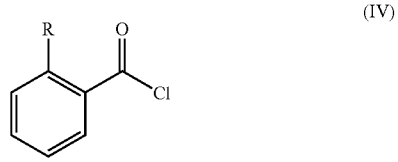

(IV)

in which
R$^1$ represents trifluoromethyl, chlorine, bromine or iodine,
if appropriate in the presence of an acid binder and if appropriate in the presence of a diluent.

Finally, it has been found that the novel phenylbenzamides of the formula (I) have very good microbicidal properties and can be used for controlling unwanted microorganisms both in crop protection and in the protection of materials.

Surprisingly, the phenylbenzamides of the formula (I) according to the invention have considerably better fungicidal activity than the constitutionally most similar active compounds of the prior art having the same direction of action.

The formula (I) provides a general definition of the phenylbenzamides according to the invention.

Preference is given to phenylbenzamides of the formula (I) in which R$^2$ represents hydrogen.

Preference is given to phenylbenzamides of the formula (I) in which R$^2$ represents methyl.

Preference is given to phenylbenzamides of the formula (I) in which R$^2$ represents ethyl.

Preference is given to phenylbenzamides of the formula (I) in which R$^1$ represents tri-fluoromethyl or iodine.

According to the invention, the formula (I) embraces the following phenylbenzamides:
N-[2-(1,3-dimethylbutyl)phenyl]-2-(trifluoromethyl)benzamide,
N-[2-(1,3-dimethylbutyl)phenyl]-2-chlorobenzamide,
N-[2-(1,3-dimethylbutyl)phenyl]-2-bromobenzamide,
N-[2-(1,3-dimethylbutyl)phenyl]-2-iodobenzamide,
2-(trifluoromethyl)-N-[2-(1,3,3-trimethylbutyl)phenyl]benzamide,
2-chloro-N-[2-(1,3,3-trimethylbutyl)phenyl]benzamide,
2-bromo-N-[2-(1,3,3-trimethylbutyl)phenyl]benzamide, 2-iodo-N-[2-(1,3,3-trimethylbutyl)phenyl]benzamide,
[2-(trifluoromethyl)phenyl]-N-[2-(1,3,3-trimethylpentyl) phenyl]carboxamide,
(2-chlorophenyl)-N-[2-(1,3,3-trimethylpentyl)phenyl]carboxamide,
(2-bromophenyl)-N-[2-(1,3,3-trimethylpentyl)phenyl]carboxamide,
(2-iodophenyl)-N-[2-(1,3,3-trimethylpentyl)phenyl]carboxamide.

Using aniline, 4-methyl-1-pentene and 2-(trifluoromethyl)benzoyl chloride as starting materials, the course of the process according to the invention can be illustrated by the following formula scheme:

a)
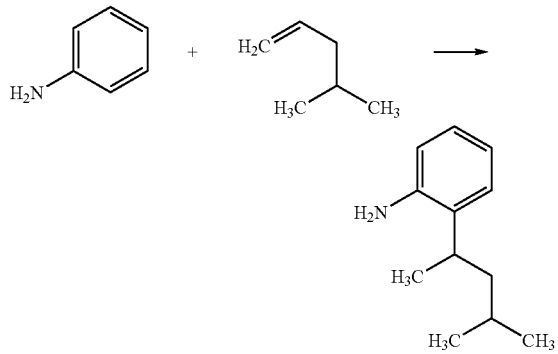

b)
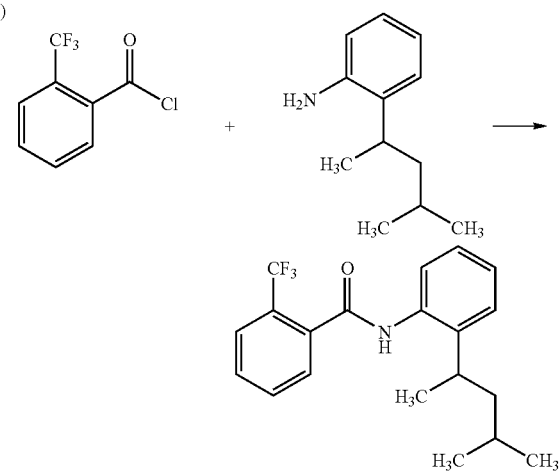

The components aniline and the alkenes of the formula (II), that is 4-methyl-1-pentene, 4,4-dimethyl-1-pentene and 4,4-dimethyl-1-hexene, required as starting materials for carrying out the first step of the process according to the invention are generally known chemicals for synthesis and commercially available.

The benzoyl chlorides of the formula (IV), that is 2-(trifluoromethyl)benzoyl chloride, 2-chlorobenzoyl chloride, 2-bromobenzoyl chloride and 2-iodobenzoyl chloride, required as starting materials for carrying out the second step of the process according to the invention are generally known chemicals for synthesis and commercially available.

The alkylphenylamine derivatives of the formula (III) obtained in the first step (a) of the process according to the invention are novel and also form part of the subject-matter of the present invention.

The alkylphenylamine derivatives of the formula (III) according to the invention are 2-(1,3-dimethylbutyl)phenylamine, 2-(1,3,3-trimethylbutyl)phenylamine and 2-(1,3,3-trimethylpentyl)phenylamine.

Suitable bases for carrying out the first step (a) of the process according to the invention are all inorganic and organic bases customary for such reactions. Preference is given to using aluminium granules (cf DE-A 27 30 620).

Suitable Lewis acids for carrying out the first step (a) of the process according to the invention are all compounds customary for such reactions. Preference is given to using aluminium chloride or iron chloride, particularly preferably aluminium chloride (cf. DE-A 27 30 620).

Suitable acid binders for carrying out the second step (b) of the process according to the invention are all inorganic and organic bases customary for such reactions. Preference is given to using alkaline earth metal or alkali metal hydroxides, such as sodium hydroxide, calcium hydroxide, potassium hydroxide or else ammonium hydroxide, alkali metal carbonates, such as sodium carbonate, potassium carbonate, potassium bicarbonate, sodium bicarbonate, alkali metal or alkaline earth metal acetates, such as sodium acetate, potassium acetate, calcium acetate, and also tertiary amines, such as trimethylamine, triethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU). Particular preference is given to using potassium carbonate.

Suitable diluents for carrying out the second step (b) of the process according to the invention are all customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decalin; chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisol; nitrites, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate; sulphoxides, such as dimethyl sulphoxide; or sulphones, such as sulpholane. Particular preference is given to using acetonitrile.

When carrying out the first step (a) of the process according to the invention, the reaction temperatures can in each case be varied within a relatively wide range. In general, the first step is carried out at temperatures between 100° C. and 300° C., preferably between 150° C. and 280° C., particularly preferably between 200° C. and 260° C.

The process according to the invention is generally in each case carried out under elevated pressure of from 1 bar to 250 bar. The operations are preferably carried out under elevated pressure of from 50 bar to 150 bar.

When carrying out the second step (b) of the process according to the invention, the reaction temperatures can be varied within a relatively wide range. In general, the second step is carried out at temperatures between −20° C. and 180° C., preferably between 10° C. and 50° C.

The second step (b) of the process according to the invention is generally in each case carried out under atmospheric pressure. However, in each case it is also possible to operate under elevated or reduced pressure.

When carrying out the first step (a) of the process according to the invention, in general from 1 to 10 mol, preferably from 1.5 to 5 mol, particularly preferably from 2 to 2.5 mol, of 4-methyl-1-pentene are employed per mole of aniline. However, it is also possible to employ the reaction components in other ratios. Work-up is carried out by customary methods. In general, the reaction mixture is stirred with toluene and aqueous base, and the organic phase is separated off and, after drying, concentrated under reduced pressure. The residue that remains may, if required, be freed of any impurities that may still be present using customary methods, such as chromatography, distillation or recrystallization.

When carrying out the second step (b) of the process according to the invention, in general 1 mol or else an excess of 2-(1,3-dimethylbutyl)phenylamine of the formula (II) is employed per mole of benzoyl chloride of the formula (III). However, it is also possible to employ the reaction components in other ratios. Work-up is carried out by customary methods. In general, the reaction mixture is extracted with water and the organic phase is separated off, dried and concentrated under reduced pressure. The residue that remains may, if required, be freed of any impurities that may still be present using customary methods, such as chromatography or recrystallization.

The substances according to the invention have potent microbicidal activity and can be employed for controlling unwanted microorganisms, such as fungi and bacteria, in crop protection and in the protection of materials.

Fungicides can be employed in crop protection for controlling Plasmodiophoromycetes, Oomycetes, Chytridiomycetes, Zygomycetes, Ascomycetes, Basidiomycetes and Deuteromycetes.

Bactericides can be employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above may be mentioned as examples, but not by way of limitation:

Xanthomonas species, such as, for example, Xanthomonas campestris pv. oryzae;
Pseudomonas species, such as, for example, Pseudomonas syringae pv. lachrymans;
Erwinia species, such as, for example, Erwinia amylovora;
Pythium species, such as, for example, Pythium ultimum;
Phytophthora species, such as, for example, Phytophthora infestans;
Pseudoperonospora species, such as, for example, Pseudoperonospora humuli or Pseudoperonospora cubensis;
Plasmopara species, such as, for example, Plasmopara viticola; Bremia species, such as, for example, Bremia lactucae;
Peronospora species, such as, for example, Peronospora pisi or P. brassicae;
Erysiphe species, such as, for example, Erysiphe graminis;
Sphaerotheca species, such as, for example, Sphaerotheca fuliginea;
Podosphaera species, such as, for example, Podosphaera leucotricha;
Venturia species, such as, for example, Venturia inaequalis;
Pyrenophora species, such as, for example, Pyrenophora teres or P. graminea (conidia form: Drechslera, syn: Helminthosporium);
Cochliobolus species, such as, for example, Cochliobolus sativus (conidia form: Drechslera, syn: Helminthosporium);
Uromyces species, such as, for example, Uromyces appendiculatus;
Puccinia species, such as, for example, Puccinia recondita;
Sclerotinia species, such as, for example, Sclerotinia sclerotiorum;
Tilletia species, such as, for example, Tilletia caries;
Ustilago species, such as, for example, Ustilago nuda or Ustilago avenae;
Pellicularia species, such as, for example, Pellicularia sasakii;
Pyricularia species, such as, for example, Pyricularia oryzae;
Fusarium species, such as, for example, Fusarium culmorum;
Botrytis species, such as, for example, Botrytis cinerea;
Septoria species, such as, for example, Septoria nodorum;
Leptosphaeria species, such as, for example, Leptosphaeria nodorum;
Cercospora species, such as, for example, Cercospora canescens;
Alternaria species, such as, for example, Alternaria brassicae; and
Pseudocercosporella species, such as, for example, Pseudocercosporella herpotrichoides.

The active compounds according to the invention also have very good fortifying action in plants. Accordingly, they can be used for mobilizing the defences of the plant against attack by unwanted microorganisms.

In the present context, plant-fortifying (resistance-inducing) substances are to be understood as meaning those substances which are capable of stimulating the defence system of plants such that, when the treated plants are subsequently inoculated with unwanted microorganisms, they show substantial resistance against these microorganisms.

In the present case, unwanted microorganisms are to be understood as meaning phytopathogenic fungi, bacteria and viruses. Accordingly, the substances according to the invention can be used to protect plants for a certain period after the treatment against attack by the pathogens mentioned. The period for which protection is provided generally extends over 1 to 10 days, preferably 1 to 7 days, after the treatment of the plants with the active compounds.

The fact that the active compounds are well tolerated by plants at the concentrations required for controlling plant diseases permits the treatment of above-ground parts of plants, of propagation stock and seeds, and of the soil.

The active compounds according to the invention are also suitable for increasing the yield of crops. In addition, they show reduced toxicity and are well tolerated by plants.

At certain concentrations and application rates, the active compounds according to the invention can also be used as herbicides, for influencing plant growth and for controlling animal pests. They can also be used as intermediates and precursors for the synthesis of further active compounds.

The active compounds according to the invention can be used to treat all plants and parts of plants. By plants are understood here all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including the plant varieties which can or cannot be protected by varietal property rights. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes.

Parts of plants also include harvested plants and vegetative and generative propagation material, for example seedlings, tubers, rhizomes, cuttings and seeds.

The treatment of the plants and the parts of plants with the active compounds according to the invention is carried out directly or by action on their surroundings, habitat or storage space, according to customary treatment methods, for example by dipping, spraying, evaporating, atomizing, broadcasting, spreading-on and, in the case of propagation material, in particular in the case of seeds, furthermore by one- or multi-layer coating.

In the protection of materials, the compounds according to the invention can be employed for protecting industrial materials against infection with, and destruction by, undesired microorganisms.

Industrial materials in the present context are understood as meaning non-living materials which have been prepared for use in industry. For example, industrial materials which are intended to be protected by active compounds according to the invention from microbial change or destruction can be adhesives, sizes, paper and board, textiles, leather, wood, paints and plastic articles, cooling lubricants and other materials which can be infected with, or destroyed by, microorganisms. Parts of production plants, for example cooling-water circuits, which may be impaired by the proliferation of microorganisms may also be mentioned within the scope of the materials to be protected. Industrial materials which may be mentioned within the scope of the present invention are preferably adhesives, sizes, paper and board, leather, wood, paints, cooling lubricants and heat-transfer liquids, particularly preferably wood.

Microorganisms capable of degrading or changing the industrial materials which may be mentioned are, for example, bacteria, fungi, yeasts, algae and slime organisms. The active compounds according to the invention preferably act against fungi, in particular moulds, wood-discolouring and wood-destroying fungi (Basidiomycetes), and against slime organisms and algae.

Microorganisms of the following genera may be mentioned as examples:
*Alternaria*, such as *Alternaria tenuis*,
*Aspergillus*, such as *Aspergillus niger*,
*Chaetomium*, such as *Chaetomium globosum*,
*Coniophora*, such as *Coniophora puetana*,
*Lentinus*, such as *Lentinus tigrinus*,
*Penicillium*, such as *Penicillium glaucum*,
*Polyporus*, such as *Polyporus versicolor*,
*Aureobasidium*, such as *Aureobasidium pullulans*,
*Sclerophoma*, such as *Sclerophoma pityophila*,
*Trichoderma*, such as *Trichoderma viride*,
*Escherichia*, such as *Escherichia coli*,
*Pseudomonas*, such as *Pseudomonas aeruginosa*, and
*Staphylococcus*, such as *Staphylococcus aureus*.

Depending on their particular physical and/or chemical properties, the active compounds can be converted to the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is, liquid solvents, liquefied gases under pressure, and/or solid carriers, optionally with the use of surfactants, that is emulsifiers and/or dispersants, and/or foam formers. If the extender used is water, it is also possible to employ, for example, organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as finely divided silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 percent by weight of active compound, preferably between 0.5 and 90%.

The active compounds according to the invention can be used as such or in their formulations, also in a mixture with known fungicides, bactericides, acaricides, nematicides or insecticides, to broaden, for example, the activity spectrum or to prevent development of resistance. In many cases, synergistic effects are obtained, i.e. the activity of the mixture is greater than the activity of the individual components.

Examples of suitable mixing components are the following:

Fungicides:
2-phenylphenol; 8-hydroxyquinolin sulphate;
acibenzolar-5-methyl; aldimorph; amidoflumet; ampropylfos; ampropylfos-potassium; andoprim; anilazine; azaconazole; azoxystrobin;
benalaxyl; benodanil; benomyl; benthiavalicarb-isopropyl; benzamacril; benzamacril-isobutyl; bilanafos; binapacryl; biphenyl; bitertanol; blasticidin-S; bromuconazole; bupirimate; buthiobate; butylamine;

calcium polysulphide; capsimycin; captafol; captan; carbendazim; carboxin; carpropamid; carvone; chinomethionat; chlobenthiazone; chlorfenazole; chloroneb; chlorothalonil; chlozolinate; clozylacon; cyazofamid; cyflufenamid; cymoxanil; cyproconazole; cyprodinil; cyprofuram;

Dagger G; debacarb; dichlofluanid; dichlone; dichlorophen; diclocymet; diclomezine; dicloran; diethofencarb; difenoconazole; diflumetorim; dimethirimol; dimethomorph; dimoxystrobin; diniconazole; diniconazole-M; dinocap; diphenylamine; dipyrithione; ditalimfos; dithianon; dodine; drazoxolon;

edifenphos; epoxiconazole; ethaboxam; ethirimol; etridiazole;

famoxadone; fenamidone; fenapanil; fenarimol; fenbuconazole; fenfuram; fenhexamid; fenitropan; fenoxanil; fenpiclonil; fenpropidin; fenpropimorph; ferbam; fluazinam; flubenzinine; fludioxonil; flumetover; flumorph; fluoromide; fluoxastrobin; fluquinconazole; flurprimidol; flusilazole; flusulfamide; flutolanil; flutriafol; folpet; fosetyl-Al; fosetyl-sodium; fuberidazole; furalaxyl; furametpyr; furcarbanil; furmecyclox;

guazatine; hexachlorobenzene; hexaconazole; hymexazole;

imazalil; imibenconazole; iminoctadine triacetate; iminoctadine tris(albesil); iodocarb; ipconazole; iprobenfos; iprodione; iprovalicarb; irumamycin; isoprothiolane; isovaledione;

kasugamycin; kresoxim-methyl;

mancozeb; maneb; meferimzone; mepanipyrim; mepronil; metalaxyl; metalaxyl-M; metconazole; methasulfocarb; methfuroxam; metiram; metominostrobin; metsulfovax; mildiomycin; myclobutanil; myclozolin;

natamycin; nicobifen; nitrothal-isopropyl; noviflumuron; nuarimol;

ofurace; orysastrobin; oxadixyl; oxolinic acid; oxpoconazole; oxycarboxin; oxyfenthiin;

paclobutrazole; pefurazoate; penconazole; pencycuron; phosdiphen; phthalide; picoxystrobin; piperalin; polyoxins; polyoxorim; probenazole; prochloraz; procymidone; propamocarb; propanosine-sodium; propiconazole; propineb; proquinazid; prothioconazole; pyraclostrobin; pyrazophos; pyrifenox; pyrimethanil; pyroquilon; pyroxyfur; pyrrolenitrine; quinconazole; quinoxyfen; quintozene;

simeconazole; spiroxamine; sulphur;

tebuconazole; tecloftalam; tecnazene; tetcyclacis; tetraconazole; thiabendazole; thicyofen; thifluzamide; thiophanate-methyl; thiram; tioxymid; tolclofos-methyl; tolylfluanid; triadimefon; triadimenol; triazbutil; triazoxide; tricyclamide; tricyclazole; tridemorph; trifloxystrobin; triflumizole; triforine; triticonazole;

uniconazole; validamycin A; vinclozolin; zineb; ziram; zoxamide;

(2S)-N-[2-[4-[[3-(4-chlorophenyl)-2-propynyl]oxy]-3-methoxyphenyl]ethyl]-3-methyl-2-[(methylsulphonyl)amino]butanamide;

1-(1-naphthalenyl)-1H-pyrrole-2,5-dione;

2,3,5,6-tetrachloro-4-(methylsulphonyl)pyridine;

2-amino-4-methyl-N-phenyl-5-thiazolecarboxamide;

2-chloro-N-(2,3-dihydro-1,1,3-trimethyl-1H-inden-4-yl)-3-pyridinecarboxamide;

3,4,5-trichloro-2,6-pyridinedicarbonitrile;

actinovate;

cis-1-(4-chlorophenyl)-2-(1H-1,2,4-triazol-1-yl)cycloheptanol;

methyl 1-(2,3-dihydro-2,2-dimethyl-1H-inden-1-yl)-1H-imidazole-5-carboxylate; monopotassium carbonate;

N-(6-methoxy-3-pyridinyl)-cyclopropanecarboxamide;

N-butyl-8-(1,1-dimethylethyl)-1-oxaspiro[4.5]decane-3-amine;

sodium tetrathiocarbonate;

and copper salts and preparations, such as Bordeaux mixture; copper hydroxide; copper naphthenate; copper oxychloride; copper sulphate; cufraneb; copper oxide; mancopper; oxine-copper.

Bactericides:

bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:

abamectin, acephate, acetamiprid, acrinathrin, alanycarb, aldicarb, aldoxycarb, alpha-cypermethrin, alphamethrin, amitraz, avermectin, AZ 60541, azadirachtin, azamethiphos, azinphos A, azinphos M, azocyclotin,

*Bacillus popilliae, Bacillus sphaericus, Bacillus subtilis, Bacillus thuringiensis*, baculoviruses, *Beauveria bassiana, Beauveria tenella*, bendiocarb, benfuracarb, bensultap, benzoximate, betacyfluthrin, bifenazate, bifenthrin, bioethanomethrin, biopermethrin, bistrifluron, BPMC, bromophos A, bufencarb, buprofezin, butathiofos, butocarboxim, butylpyridaben, cadusafos, carbaryl, carbofuran, carbophenothion, carbosulphan, cartap, chloethocarb, chlorethoxyfos, chlorfenapyr, chlorfenvinphos, chlorfluazuron, chlormephos, chlorpyrifos, chlorpyrifos M, chlovaporthrin, chromafenozide, cis-resmethrin, cispermethrin, clocythrin, cloethocarb, clofentezine, clothianidine, cyanophos, cycloprene, cycloprothrin, cyfluthrin, cyhalothrin, cyhexatin, cypermethrin, cyromazine, deltamethrin, demeton M, demeton S, demeton-5-methyl, diafenthiuron, diazinon, dichlorvos, dicofol, diflubenzuron, dimethoat, dimethylvinphos, diofenolan, disulphoton, docusat-sodium, dofenapyn, eflusilanate, emamectin, empenthrin, endosulphan, *Entomopfthora* spp., esfenvalerate, ethiofencarb, ethion, ethoprophos, etofenprox, etoxazole, etrimfos, fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazuron, flubrocythrinate, flucycloxuron, flucythrinate, flufenoxuron, flumethrin, flutenzine, fluvalinate, fonophos, fosmethilan, fosthiazate, fubfenprox, furathiocarb, granulosis viruses, halofenozide, HCH, heptenophos, hexaflumuron, hexythiazox, hydroprene, imidacloprid, indoxacarb, isazofos, isofenphos, isoxathion, ivennectin, nuclear polyhedrosis viruses, lambda-cyhalothrin, lufenuron, malathion, mecarbam, metaldehyde, methamidophos, *Metharhizium anisopliae, Metharhizium flavoviride*, methidathion, methiocarb, methoprene, methomyl, methoxyfenozide, metolcarb, metoxadiazone, mevinphos, milbemectin, milbemycin, monocrotophos, naled, nitenpyram, nithiazine, novaluron, omethoate, oxamyl, oxydemethon M, Paecilomyces fumosoroseus, parathion A, parathion M, permethrin, phenthoate, phorat, phosalone, phosmet, phosphamidon, phoxim, pirmicarb, pirimiphos A, pirimiphos M, profenofos, promecarb, propargite, propoxur, prothiofos, prothoat, pymetrozine, pyraclofos, pyresmethrin, pyrethrum, pyridaben, pyridathion, pyrimidifen, pyriproxyfen, quinalphos, ribavirin, salithion, sebufos, silafluofen, spinosad, spirodiclofen, sulphotep, sulprofos, tau-fluvalinate, tebufenozide, tebufenpyrad, tebupirimiphos, teflubenzuron, tefluthrin, temephos, temivinphos, terbufos, tetrachlorvinphos, tetradifon thetacypermethrin, thiacloprid, thiamethoxam, thiapronil, thiatriphos, thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb, vamidothion, vaniliprole, *Verticillium lecanii*, YI 5302, Zeta-cypermethrin, Zolaprofos (1R-cis)-[5-(phenylmethyl)-3-furanyl]methyl 3-[(dihydro-2-oxo-3(2H)-furanylidene)methyl]-2,2-dimethylcyclopropanecarboxylate, (3-phenoxyphenyl)methyl 2,2,3,3-tetramethylcyclopropanecarboxylate, 1-[(2-chloro-5-thiazolyl)methyl]tetrahydro-3,5-dimethyl-N-nitro-1,3,5-triazine-2(1H)-imine, 2-(2-chloro-6-fluorophenyl)-4-[4-(1,1-dimethylethyl)phenyl]-4,5-dihydrooxazole, 2-(acetyloxy)-3-dodecyl-1,4-naphthalenedione, 2-chloro-N-[[[4-(1-phenylethoxy)phenyl]amino]carbonyl] benzamide, 2-chloro-N-[[[4-(2,2-dichloro-1,1-difluoroethoxy)phenyl] amino]carbonyl]-benzamide, 3-methylphenyl propylcarbamate 4-[4-(4-ethoxyphenyl)-4-methylpentyl]-1-fluoro-2-phenoxybenzene, 4-chloro-2-(1,1-dimethylethyl)-5-[[2-(2,6-dimethyl-4-phenoxyphenoxy)ethyl]thio]-3(2H)-pyridazinone, 4-chloro-2-(2-chloro-2-methylpropyl)-5-[(6-iodo-3-pyridinyl)methoxy]-3(2H)-pyrida 4-chloro-5-[(6-chloro-3-pyridinyl)methoxy]-2-(3,4-dichlorophenyl)-3(2H)-pyridazinone,

*Bacillus thuringiensis* strain EG-2348,

[2-benzoyl-1-(1,1-dimethylethyl)hydrazinobenzoic acid, 2,2-dimethyl-3-(2,4-dichlorophenyl)-2-oxo-1-oxaspiro[4.5] dec-3-en-4-yl butanoate,

[3-[(6-chloro-3-pyridinyl)methyl]-2-thiazolidinylidene]cyanamide, dihydro-2-(nitromethylene)-2H-1,3-thiazine-3(4H)carboxaldehyde, ethyl[2-[[1,6-dihydro-6-oxo-1-(phenyhnethyl)-4-pyridazinyl]oxy]ethyl]carbamate, N-(3,4,4-trifluoro-1-oxo-3-butenyl)glycine, N-(4-chlorophenyl)-3-[4-(difluoromethoxy)phenyl]-4,5-dihydro-4-phenyl-1H-pyrazole-1-carboxamide, N-[(2-chloro-5-thiazolyl)methyl]-N'-methyl-N"-nitroguanidine, N-methyl-N'-(1-methyl-2-propenyl)-1,2-hydrazinedicarbothioamide, N-methyl-N'-2-propenyl-1,2-hydrazinedicarbothioamide, O,O-diethyl[2-(dipropylamino)-2-oxoethyl]ethylphosphoramidothioate, N-cyanomethyl-4-trifluoromethylnicotinamide, 3,5-dichloro-1-(3,3-dichloro-2-propenyloxy)-4-[3-(5-trifluoromethylpyridine-2-yloxy)propoxy]benzene.

A mixture with other known active compounds, such as herbicides, or with fertilizers and growth regulators, is also possible.

In addition, the compounds of the formula (I) according to the invention also have very good antimycotic activity. They have a very broad antimycotic activity spectrum in particular against dermatophytes and yeasts, moulds and diphasic fungi, (for example against *Candida* species, such as *Candida albicans, Candida glabrata*), and Epidermophyton floccosum, *Aspergillus* species, such as *Aspergillus niger* and *Aspergillus fumigatus, Trichophyton* species, such as *Trichophyton mentagrophytes, Microsporon* species such as *Microsporon canis* and audouinii. The list of these fungi by no means limits the mycotic spectrum covered, but is only for illustration.

The active compounds can be used as such, in the form of their formulations or the use forms prepared therefrom, such as ready-to-use solutions, suspensions, wettable powders, pastes, soluble powders, dusts and granules. Application is carried out in a customary manner, for example by watering, spraying, atomizing, broadcasting, dusting, foaming, spreading, etc. It is furthermore possible to apply the active compounds by the ultra-low volume method, or to inject the active compound preparation or the active compound itself into the soil. It is also possible to treat the seeds of the plants.

When using the active compounds according to the invention as fungicides, the application rates can be varied within a relatively wide range, depending on the kind of application. For the treatment of parts of plants, the active compound application rates are generally between 0.1 and 10,000 g/ha, preferably between 10 and 1000 g/ha. For seed dressing, the active compound application rates are generally between 0.001 and 50 g per kilogram of seed, preferably between 0.01 and 10 g per kilogram of seed. For the treatment of the soil, the active compound application rates are generally between 0.1 and 10,000 g/ha, preferably between 1 and 5000 g/ha.

As already mentioned above, it is possible to treat all plants and their parts with active compounds according to the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof are treated. The term "parts" or "parts of plants" or "plant parts" has been explained above.

Particularly preferably, plants of the plant cultivars which are in each case commercially available or in use are treated according to the invention. Plant cultivars are to be understood as meaning plants having new properties ("traits") and which have been obtained by conventional breeding, by mutagenesis or by recombinant DNA techniques. They can be cultivars, varieties, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The transgenic plants or plant cultivars (i.e. those obtained by genetic engineering) which are preferably treated according to the invention include all plants which, in the genetic modification, received genetic material which imparted particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, oilseed rape and also fruit plants (with the fruits apples, pears, citrus fruits and grapes), and particular emphasis is given to maize, soya beans, potatoes, cotton and oilseed rape. Traits that are emphasized are in particular increased defence of the plants against insects by toxins formed in the plants, in particular those formed in the plants by the genetic material from *Bacillus thuringiensis* (for example by the genes CryIA(a), CryIA(b), CryIA(c), CryIIA, CryIIA, CryIIIB2, Cry9c Cry2Ab, Cry3Bb and CryIF and also combinations thereof) (hereinbelow referred to as "Bt plants"). Traits that are also particularly emphasized are the increased defence of the plants to fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucoton® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylurea, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plants will be developed and/or marketed in the future.

The plants listed can be treated according to the invention in a particularly advantageous manner with the compounds of the formula (I) according to the invention or the active compound mixtures according to the invention. The preferred ranges stated above for the active compounds or mixtures also apply to the treatment of these plants. Particular emphasis is given to the treatment of plants with the compounds and mixtures specifically mentioned in the present text.

The preparation and the use of the active compounds according to the invention is illustrated by the examples below.

PREPARATION EXAMPLES

Example 1

Preparation of 2-(1,3-dimethylbutyl)phenylamine of the formula (III)

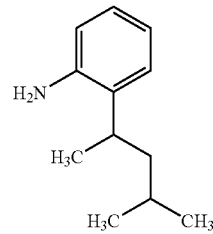

In a steel autoclave, a mixture of 62.8 g (0.67 mol) of aniline, 132.8 g (1.58 mol) of 4-methylpent-1-ene, 1.82 g of aluminium granules and 5.58 g (41.8 mmol) of aluminium chloride is heated to 255° C. The reaction mixture is kept at this temperature and under autogenous pressure for 10 h.

For work-up, the contents of the autoclave are, after cooling and venting, transferred quantitatively into a new vessel using toluene, and stirred with 80 ml of 40% strength aqueous sodium hydroxide solution and 100 ml of water at 30-40° C. for 15 min. The organic phase is separated off, washed with water and dried over potassium carbonate. The toluene is removed using a rotary evaporator and the residue is then subjected to fractional distillation.

This gives 43.9 g (33%) of 2-(1,3-dimethylbutyl)phenylamine as a colourless oil (boiling range 73-85° C., 0.3 mbar).

Example 2

N-[2-(1,3-dimethylbutyl)phenyl]-2-(trifluoromethyl)benzamide

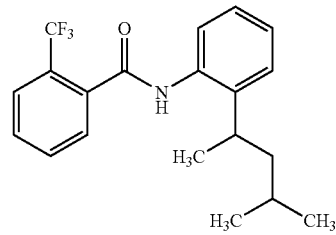

5.32 g (30 mmol) of 2-(1,3-dimethylbutyl)phenylamine (Example 1) and 6.26 g (30 mmol) of 2-(trifluoromethyl)benzoyl chloride are added dropwise to a suspension of 4.15 g of potassium carbonate in 200 ml of acetonitrile. The reaction mixture is stirred for 10 h.

For work-up, 200 ml of water are added to the reaction solution, and the mixture is extracted with ethyl acetate. The organic phases are dried with sodium sulphate and concentrated. The residue is chromatographed on silica gel (gradient cyclohexane 100% to cyclohexane/ethyl acetate 1:4).

This gives 5.00 g (46%) of N-[2-(1,3-dimethylbutyl) phenyl]-2-(trifluoromethyl)benzamide of logP (pH 2.3)=4.09.

Example 3

N-[2-(1,3-dimethylbutyl)phenyl]-2-iodobenzamide

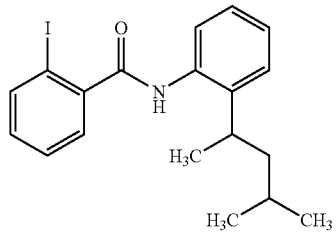

3.55 g (20 mmol) of 2-(1,3-dimethylbutyl)phenylamine (Example 1) and 5.33 g (20 mmol) of 2-iodobenzoyl chloride are added dropwise to a suspension of 2.76 g of potassium carbonate in 100 ml of acetonitrile. The reaction mixture is stirred for 10 h.

For work-up, 100 ml of water are added to the reaction solution, and the mixture is extracted with ethyl acetate. The organic phases are dried with sodium sulphate and concentrated. The residue is chromatographed on silica gel (gradient cyclohexane 100% to cyclohexane/ethyl acetate 1:4).

This gives 7.00 g (83%) of N-[2-(1,3-dimethylbutyl) phenyl]-2-iodobenzamide of logP (pH 2.3)=4.12.

Analogously to the examples mentioned above, the following compounds are obtained starting with aniline and 4-methylpent-1-ene and 2-chlorobenzoyl chloride and 2-bromobenzoyl chloride, respectively:

Example 4

N-[2-(1,3-dimethylbutyl)phenyl]-2-chlorobenzamide

[logP (pH 2.3)=3.98]

Example 5

N-[2-(1,3-dimethylbutyl)phenyl]-2-bromobenzamide

[logP (pH 2.3)=4.01]

Moreover, analogously to the examples mentioned above, the following compounds are obtained starting with aniline and 4,4-dimethyl-1-pentene and 2-(trifluoromethyl)benzoyl chloride, 2-chlorobenzoyl chloride, 2-bromobenzoyl chloride and 2-iodobenzoyl chloride, respectively:

Example 6

2-(trifluoromethyl)-N-[2-(1,3,3-trimethylbutyl)phenyl]benzamide

[logP (pH 2.3)=4.36]

Example 7

2-chloro-N-[2-(1,3,3-trimethylbutyl)phenyl]benzamide

[logP (pH 2.3)=4.25]

Example 8

2-bromo-N-[2-(1,3,3-trimethylbutyl)phenyl]benzamide

[logP (pH 2.3)=4.29]

Example 9

2-iodo-N-[2-(1,3,3-trimethylbutyl)phenyl]benzamide

[logP (pH 2.3)=4.40]

Example 10

(2-iodophenyl)-N-[2-(1,3,3-trimethylpentyl)phenyl] carboxamide.

[logP (pH 2.3)=4.71]

Example 11

[2-(trifluoromethyl)phenyl]-N-[2-(1,3,3-trimethylpentyl)phenyl]carboxamide

[logP (pH 2.3)=4.68]

Example 12

(2-chlorophenyl)-N-[2-(1,3,3-trimethylpentyl)phenyl]carboxamide.

[logP (pH 2.3)=4.60]

Example 13

(2-bromophenyl)-N-[2-(1,3,3-trimethylpentyl)phenyl]carboxamide

[logP (pH 2.3)=4.63]

The logP values given in the Preparation Examples were determined in accordance with EEC Directive 79/831 Annex V.A8 by HPLC (High Performance Liquid Chromatography) using a reversed-phase column (C 18). Temperature: 43° C.

Mobile phases for the determination in the acidic range: 0.1% aqueous phosphoric acid, acetonitrile; linear gradient from 10% acetonitrile to 90% acetonitrile.

Calibration was carried out using unbranched alkan-2-ones (having 3 to 16 carbon atoms) with known logP values (determination of the logP values by the retention times using linear interpolation between two successive alkanols).

Use Examples

Example A

*Sphaerotheca* Test (Cucumber)/Protective

Solvents: 24.5 parts by weight of acetone 24.5 parts by weight of dimethylacetamide Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of *Sphaerotheca fuliginea*. The plants are then placed in a greenhouse at about 23° C. and a relative atmospheric humidity of about 70%.

Evaluation is carried out 7 days after the inoculation. 0% means an efficacy which corresponds to that of the control, whereas an efficacy of 100% means that no infection is observed.

Active compounds, application rates and test results are shown in the table below.

TABLE A

Sphaerotheca test (cucumber)/protective

| Active compound | Application rate of active compound in g/ha | Efficacy in % |
|---|---|---|
| 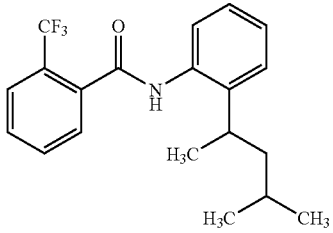 | 100 | 100 |
| 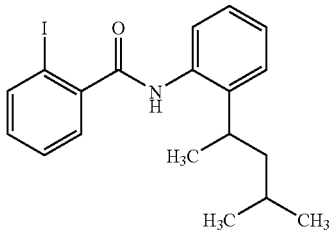 | 100 | 100 |

Example B

*Venturia* Test (Apple)/Protective

Solvents: 24.5 parts by weight of acetone 24.5 parts by weight of dimethylacetamide Emulsifier: 1.0 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous conidia suspension of the apple scab pathogen *Venturia inaequalis* and then remain in an incubation cabin at about 20° C. and 100% relative atmospheric humidity for 1 day.

The plants are then placed in a greenhouse at about 21° C. and a relative atmospheric humidity of about 90%.

Evaluation is carried out 10 days after the inoculation. 0% means an efficacy which corresponds to that of the control, whilst an efficacy of 100% means that no infection is observed.

Active compounds, application rates and test results are shown in the table below.

TABLE B

Venturia test (apple)/protective

| Active compound | Application rate of active compound in g/ha | Efficacy in % |
|---|---|---|
| 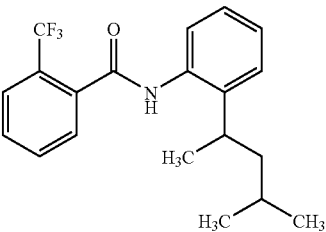 | 100 | 100 |
| 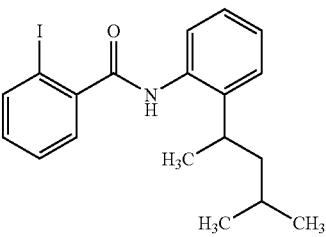 | 100 | 100 |

Example C

*Botrytis* Test (Bean)/Protective

Solvent: 49 parts by weight of N,N-dimethylformamide

Emulsifier: 1 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, 2 small pieces of agar colonized by *Botrytis cinerea* are placed onto each leaf. The inoculated plants are placed in a dark chamber at about 20° C. and 100% relative atmospheric humidity.

2 days after the inoculation, the size of the infected areas on the leaves is evaluated. 0% means an efficacy which corresponds to that of the control, whereas an efficacy of 100% means that no infection is observed.

Active compounds, application rates and test results are shown in the table below.

TABLE C

Botrytis test (bean)/protective

| Active compound | Application rate of active compound in g/ha | Efficacy in % |
|---|---|---|
| [structure: 2-CF3-benzamide with N-H linked to phenyl bearing CH(CH3)CH2CH(CH3)2 group] | 500 | 93 |
| [structure: 2-I-benzamide with N-H linked to phenyl bearing CH(CH3)CH2CH(CH3)2 group] | 500 | 93 |

Example D

*Alternaria* Test (Tomato)/Protective
Solvent: 49 parts by weight of N,N-dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young tomato plants are sprayed with the preparation of active compound at the stated application rate. 1 day after the treatment, the plants are inoculated with an aqueous spore suspension of *Alternaria solani* and then remain at 100% relative atmospheric humidity for 24 hours. The plants are then kept at about 96% relative atmospheric humidity and a temperature of 20° C.

Evaluation is carried out 7 days after the inoculation. 0% means an efficacy which corresponds to that of the control, whereas an efficacy of 100% means that no infection is observed.

Active compounds, application rates and test results are shown in the table below.

TABLE D

Alternaria test (tomato)/protective

| Active compound | Application rate of active compound in g/ha | Efficacy in % |
|---|---|---|
| [structure: 2-CF3-benzamide with N-H linked to phenyl bearing CH(CH3)CH2CH(CH3)2 group] | 750 | 100 |
| [structure: 2-I-benzamide with N-H linked to phenyl bearing CH(CH3)CH2CH(CH3)2 group] | 750 | 100 |

Example E

*Erysiphe* Test (Barley)/Protective
Solvent: 49 parts by weight of N,N-dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young cereal plants are sprayed with the preparation of active compound at the stated application rate. 1 day after the treatment, the plants are inoculated with spores of *Erysiphe graminis* f. sp. *hordei*. The plants are then placed in a greenhouse at 70% relative atmospheric humidity and a temperature of 18° C.

Evaluation is carried out 7 days after the inoculation. 0% means an efficacy which corresponds to that of the control, whereas an efficacy of 100% means that no infection is observed.

Active compounds, application rates and test results are shown in the table below.

TABLE E

Erysiphe test (barley)/protective

| Active compound | Application rate of active compound in g/ha | Efficacy in % |
|---|---|---|
| [structure: 2-CF3-benzamide with N-H linked to phenyl bearing CH(CH3)CH2CH(CH3)2 group] | 750 | 95 |

TABLE E-continued

Erysiphe test (barley)/protective

| Active compound | Application rate of active compound in g/ha | Efficacy in % |
|---|---|---|
| 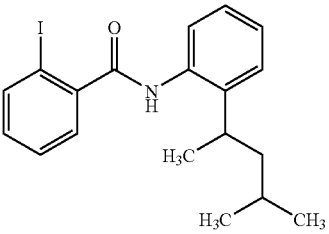 | 750 | 95 |

Example F

*Puccinia* Test (Wheat)/Protective

Solvent: 25 parts by weight of N,N-dimethylacetamide
Emulsifier: 0.6 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are inoculated with a spore suspension of *Puccinia recondita* in a 0.1% strength aqueous agar solution. After the spray coating has dried on, the plants are sprayed with the preparation of active compound at the stated application rate. The plants remain in an incubation cabin at 20° C. and 100% relative atmospheric humidity for 24 hours.

The plants are then placed in a greenhouse at a temperature of about 20° C. and a relative atmospheric humidity of 80% to promote the development of rust pustules.

Evaluation is carried out 10 days after the inoculation. 0% means an efficacy which corresponds to that of the control, whereas an efficacy of 100% means that no infection is observed.

Active compounds, application rates and test results are shown in the table below.

TABLE F

Puccinia test (wheat)/protective

| Active compound | Application rate of active compound in g/ha | Efficacy in % |
|---|---|---|
| 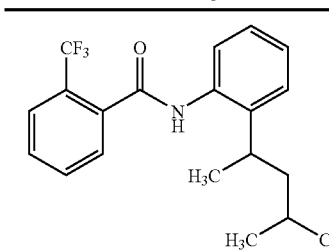 | 500 | 100 |

TABLE F-continued

Puccinia test (wheat)/protective

| Active compound | Application rate of active compound in g/ha | Efficacy in % |
|---|---|---|
| 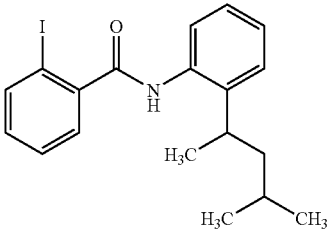 | 500 | 100 |
| 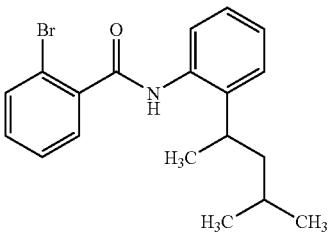 | 500 | 100 |
| 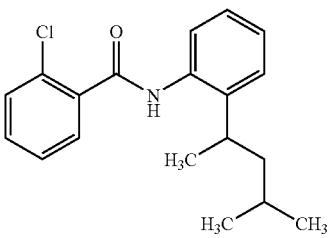 | 500 | 100 |
| 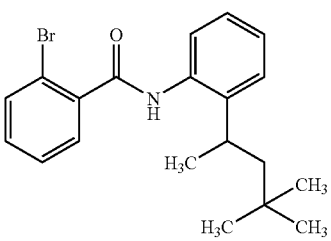 | 500 | 100 |
| 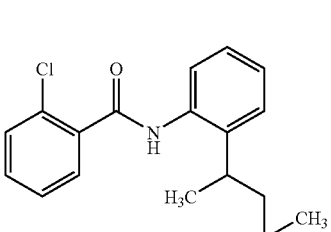 | 500 | 100 |

TABLE F-continued
Puccinia test (wheat)/protective
| Active compound | Application rate of active compound in g/ha | Efficacy in % |
|---|---|---|
| 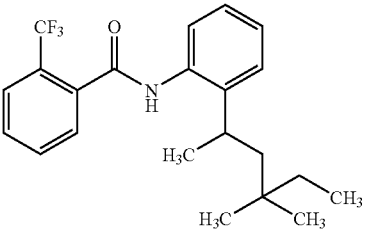 | 500 | 100 |
| 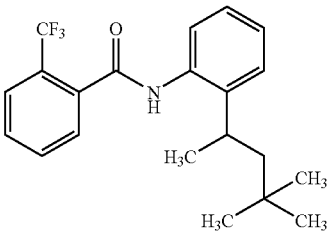 | 500 | 100 |
| 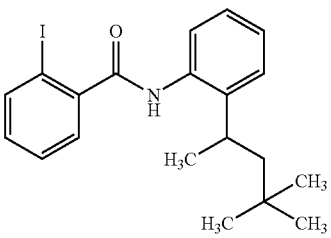 | 500 | 100 |
Example G
Comparative Experiments
In the table below, the compounds according to the invention of examples
Ex. 2
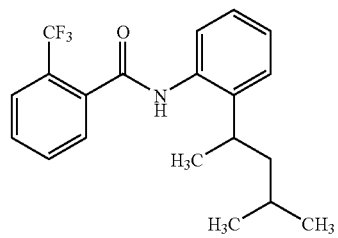
Ex. 3
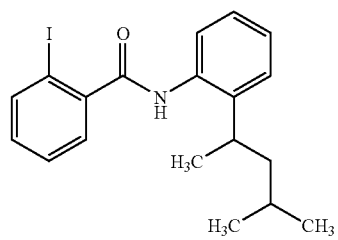
Ex. 5
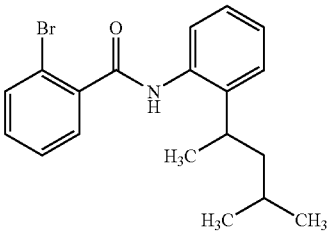
are compared to the following compounds, which are known from EP-A 0 545 099:
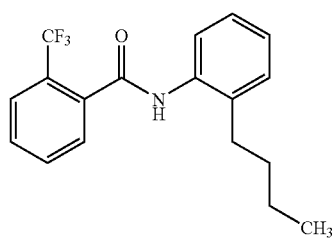
EP-A 0 545 099
Compound No. 6.3, p. 24
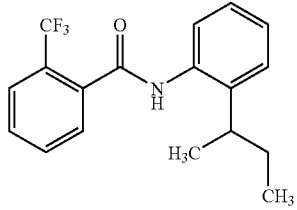
EP-A 0 545 099
Compound No. 6.4, p. 24
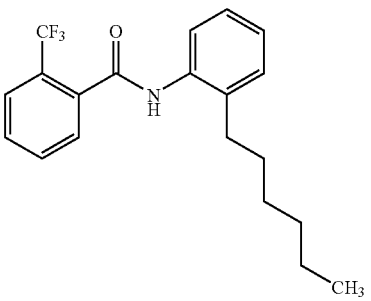
EP-A 0 545 099
Compound No. 6.9, p. 24

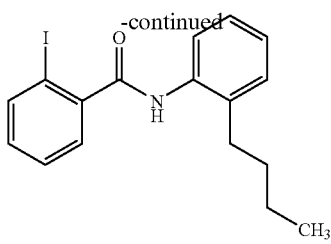

EP-A 0 545 099
Compound No. 14.3, p. 42

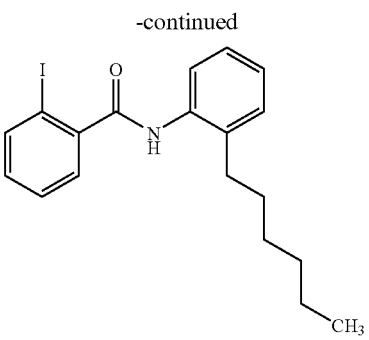

EP-A 0 545 099
Compound No. 14.9 p. 42

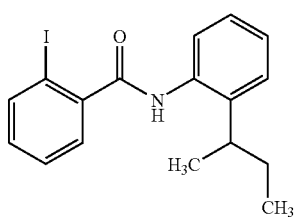

EP-A 0 545 099
Compound No. 14.4, p. 42

The compounds were tested in comparative experiments according to use examples A [*Spaerotheca* test (cucumber)/protective], D [*Alternaria* test (tomato)/protective] and E [*Erysiphe* test (barley)/protective].

In each case, the application rate was 500 ppm. The efficacy of the individual compounds in the use examples in question is given in the table below.

TABLE G

| | | Comparative experiments | | |
|---|---|---|---|---|
| | Compound according to the invention | Example A Spaerotheca test (cucumber) protective efficacy in % | Example D Alternaria test (tomato) protective efficacy in % | Example E Erysiphe test (barley) protective efficacy in % |
| Ex. 2 | (structure) | 100 | 95 | 90 |
| Ex. 3 | (structure) | 100 | 95 | 95 |
| Ex. 5 | (structure) | 95 | 90 | 30 |

TABLE G-continued

| | Comparative experiment | | |
|---|---|---|---|
| Compounds known from EP-A 0 545 099 | Example A Spaerotheca test (cucumber) protective efficacy in % | Example D Alternaria test (tomato) protective efficacy in % | Example E Erysiphe test (barley) protective efficacy in % |
| No. 6.3 (p. 24) [2-CF₃-benzamide with 2-butylphenyl] | 10 | 0 | 10 |
| No. 14.3 (p. 42) [2-I-benzamide with 2-butylphenyl] | 0 | 0 | 0 |
| No. 6.4 (p. 24) [2-CF₃-benzamide with 2-(sec-butyl)phenyl] | 30 | 30 | 0 |
| No. 14.4 (p. 42) [2-I-benzamide with 2-(sec-butyl)phenyl] | 10 | 10 | 20 |
| No. 6.9 (p. 24) [2-CF₃-benzamide with 2-hexylphenyl] | 0 | 0 | 0 |

TABLE G-continued

| No. 14.9 (p. 42) | 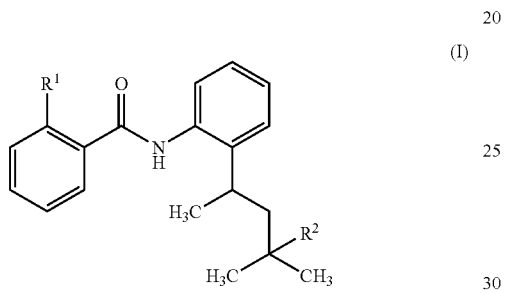 | 0 | 0 | 0 |
|---|---|---|---|---|

What is claimed is:

1. A phenylbenzamide of formula (I)

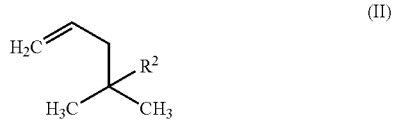

in which
R$^1$ represents trifluoromethyl, chlorine, bromine, or iodine, and
R$^2$ represents hydrogen, methyl, or ethyl.

2. A phenylbenzamide of formula (I) according to claim 1 in which R$^2$ represents hydrogen.

3. A phenylbenzamide of formula (I) according to claim 1 selected from the group consisting of
N-[2-(1,3-dimethylbutyl)phenyl]-2-(trifluoromethyl)benzamide,
N-[2-(1,3-dimethylbutyl)phenyl]-2-chlorobenzamide,
N-[2-(1,3-dimethylbutyl)phenyl]-2-bromobenzamide,
N-[2-(1,3-dimethylbutyl)phenyl]-2-iodobenzamide,
2-(trifluoromethyl)-N-[2-(1,3,3-trimethylbutyl)phenyl]benzamide,
2-chloro-N-[2-(1,3,3-trimethylbutyl)phenyl]benzamide,
2-bromo-N-[2-(1,3,3-trimethylbutyl)phenyl]benzamide, and
2-iodo-N-[2-(1,3,3-trimethylbutyl)phenyl]benzamide.

4. A process for preparing a phenylbenzamide of formula (I) according to claim 1 comprising
(a) reacting aniline with an alkene of formula (II)

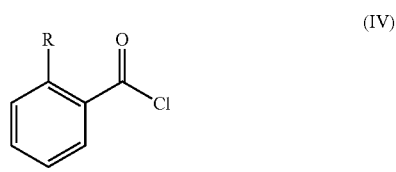

in which R$^2$ represents hydrogen, methyl, or ethyl, in the presence of a base and in the presence of a Lewis acid to form an alkylphenylamine derivative of formula (III)

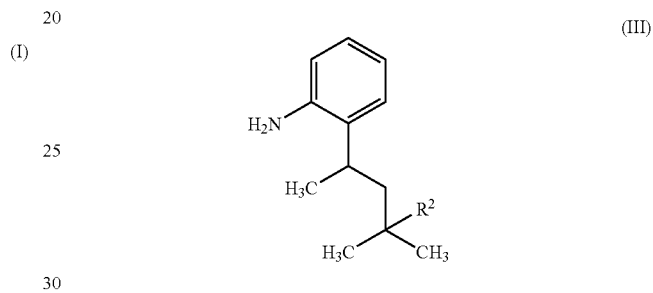

in which R$^2$ represents hydrogen, methyl, or ethyl, and
(b) reacting the alkylphenylamine derivative of formula (III) with a benzoyl chloride of formula (IV)

in which R$^1$ represents trifluoromethyl, chlorine, bromine or iodine, optionally in the presence of an acid binder and optionally in the presence of a diluent.

5. A composition for controlling fungi and bacteria in the protection of corps and materials comprising one or more phenylbenzamides of formula (I) according to claim 1 and one or more extenders and/or surfactants.

6. A method for controlling fungi and bacteria that infects crops and materials comprising applying an effective amount of one or more phenylbenzamides of formula (I) according to claim 1 to the fungi and bacteria and/or their habitat.

7. A process for preparing compositions for controlling fungi and bacteria that infects crops and materials comprising mixing one or more phenylbenzamides of formula (I) according to claim 1 with one or more extenders and/or surfactants.

8. A process for preparing a phenylamine derivative of formula (III)

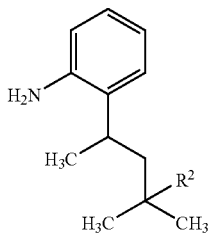

(III)

in which R² represents hydrogen, methyl, or ethyl, comprising reacting aniline with an alkene of formula (II)

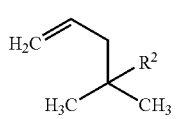

(II)

in which R² represents hydrogen, methyl, or ethyl, in the presence of a base and in the presence of a Lewis acid.

9. A method according to claim 6 wherein the fungi and bacteria are selected from *Alternaria, Aspergillus, Chaetomium, Coniophora, Lentinus, Penicillium, Polyporus, Aureobasidium, Sclerophoma, Trichoderma, Escherichia, Pseudomonas, Staphylococcus, Plasmodiophoromycetes, Oomycetes, Chytridiomycetes, Zygomycetes, Ascomycetes, Basidiomycetes, Deuteromycetes, Pseudomonadaceae, Rhizobiaceae, Enterobacteriaceae, Corynebacteriaceae, Streptomycetaceae, Xanthomonas, Pseudomonas, Erwinia, Pythium, Phytophthora, Pseudoperonospora, Plasmopara, Bremia, Peronospora, Erysiphe, Sphaerotheca, Podosphaera, Venturia, Pyrenophora, Cochliobolus, Uromyces, Puccinia, Sclerotinia, Tilletia, Ustilago, Pellicularia, Pyricularia, Fusarium, Botrytis, Septoria, Leptosphaeria, Cercospora, Alternaria,* and *Pseudocercosporella.*

* * * * *